(12) United States Patent
Lenox et al.

(10) Patent No.: US 11,170,544 B2
(45) Date of Patent: Nov. 9, 2021

(54) APPLICATION OF MACHINE LEARNING TO ITERATIVE AND MULTIMODALITY IMAGE RECONSTRUCTION

(71) Applicant: QT IMAGING, INC., Novato, CA (US)

(72) Inventors: Mark Wayne Lenox, College Station, TX (US); Nasser Charles Pirshafiey, Tiburon, CA (US); Martin Cwikla, Cotati, CA (US); Bilal Malik, Novato, CA (US); Sandeep Tiwari, Rohnert Park, CA (US)

(73) Assignee: QT IMAGING, INC., Novato, CA (US)

( * ) Notice: Subject to any disclaimer, the term of this patent is extended or adjusted under 35 U.S.C. 154(b) by 0 days.

(21) Appl. No.: 17/271,715

(22) PCT Filed: Aug. 30, 2019

(86) PCT No.: PCT/US2019/049133
§ 371 (c)(1),
(2) Date: Feb. 26, 2021

(87) PCT Pub. No.: WO2020/047456
PCT Pub. Date: May 3, 2020

(65) Prior Publication Data
US 2021/0248791 A1    Aug. 12, 2021

Related U.S. Application Data

(60) Provisional application No. 62/725,882, filed on Aug. 31, 2018.

(51) Int. Cl.
*G06T 11/00*        (2006.01)
*G06N 3/04*         (2006.01)
(Continued)

(52) U.S. Cl.
CPC .......... *G06T 11/006* (2013.01); *G06N 3/0454* (2013.01); *G06N 3/088* (2013.01);
(Continued)

(58) Field of Classification Search
CPC ............ G06T 11/006; G06T 2211/424; G06N 3/0454; G06N 3/088; G16H 30/20; G16H 30/40
See application file for complete search history.

(56) References Cited

U.S. PATENT DOCUMENTS

2010/0183217 A1   7/2010  Seung et al.
2015/0003708 A1   1/2015  Prevrhal et al.
(Continued)

FOREIGN PATENT DOCUMENTS

WO     2017/223560 A1    12/2017

OTHER PUBLICATIONS

"International Search Report and Written Opinion Issued in PCT Application No. PCT/US2019/049133", dated Dec. 31, 2019, 10 Pages.
(Continued)

*Primary Examiner* — Nay A Maung
*Assistant Examiner* — Jose M Torres
(74) *Attorney, Agent, or Firm* — Talem IP Law, LLP

(57) ABSTRACT

A method for machine learning based ultrasound image reconstruction can include receiving, at a reconstruction engine, imaging data; generating an initial estimate for a transmission image via a neural network trained (machine or self-learning) on paired transmission ultrasound and reflection ultrasound data; and performing image reconstruction using the initial estimate to generate transmission ultrasound images. The image reconstruction can generate higher quality transmission ultrasound when carried out by using the initial estimate as the starting point for iterative image
(Continued)

reconstruction and using transmission data obtained via conventional transmission ultrasound frequencies (e.g. from 0.8 MHz to 1.5 MHz).

12 Claims, 5 Drawing Sheets

(51) Int. Cl.
*G16H 30/20* (2018.01)
*G16H 30/40* (2018.01)
*G06N 3/08* (2006.01)

(52) U.S. Cl.
CPC ............. *G16H 30/20* (2018.01); *G16H 30/40* (2018.01); *G06T 2211/424* (2013.01)

(56) References Cited

U.S. PATENT DOCUMENTS

| | | |
|---|---|---|
| 2015/0279060 A1 | 10/2015 | Grady et al. |
| 2017/0200265 A1 | 7/2017 | Bhaskar et al. |
| 2017/0309019 A1 | 10/2017 | Knoll et al. |
| 2018/0336439 A1* | 11/2018 | Kliger .................. G06N 3/0472 |
| 2019/0197358 A1* | 6/2019 | Madani ................ G06N 3/0481 |
| 2019/0333219 A1* | 10/2019 | Xu ....................... G06N 3/0481 |

OTHER PUBLICATIONS

Dong Nie et al., Medical Image Synthesis with Context-Aware Generative Adversarial Networks, Dec. 16, 2016, 12 Pages.

* cited by examiner

APPLICATION OF MACHINE LEARNING TO ITERATIVE AND MULTIMODALITY IMAGE RECONSTRUCTION

CROSS-REFERENCE TO RELATED APPLICATIONS

This application is the U.S. National Stage Application of International Application No. PCT/US19/49133, filed Aug. 30, 2019, which claims the benefit of U.S. Provisional Patent Application Ser. No. 62/725,882, filed Aug. 31, 2018.

BACKGROUND

Medical imaging involves acquisition of data and image reconstruction from the data. Image reconstruction from acquired data can be treated as an inverse problem that can be solved via iterative methods. Often, an approximate solution—an assumed image or an initial estimate—is first obtained and then a better reconstruction is generated using multiple iteration steps. The iterative steps can include calculating the difference between the measured and the modeled fields utilizing all the acquired projections data, and updating the image based on comparison, resulting in progressive improvement of image quality and also reduction in reconstruction image artifacts. Image reconstruction may be carried out for imaging modalities such as magnetic resonance imaging (MRI), positron emission tomography (PET), computed tomography (CT), and ultrasound.

Ultrasound imaging uses high-frequency sound waves to view internal structures such as tissues and blood flow. A transducer transmits ultrasound waves and a receiver captures the waves after reflecting from or transmitting through the tissue. A quantitative transmission ultrasound system performs both transmission ultrasound and reflection ultrasound methods to gather data.

BRIEF SUMMARY

Machine learning based image reconstruction is described. The application of machine learning to iterative and multimodality image reconstruction can be considered "efficient" image reconstruction due to the ability to reconstruct images with fewer data points of raw data. In the context of ultrasound imaging, efficient image reconstruction does not require the low frequency transmission ultrasound data in order to reconstruct transmission images such as speed of sound images. Rather, reflection data alone or in combination with transmission data obtained via more conventional ultrasound frequencies (e.g., from 0.8 MHz to 1.5 MHz in one instance) can be used to generate suitable transmission images.

An image reconstruction system can include a communication interface receiving imaging data from a scanner system and a reconstruction engine. The reconstruction engine can include at least one neural network, a processor, and storage media storing instructions for performing image reconstruction when executed by the processor. The neural network includes a GAN-based algorithm (resulting in a "GAN-based neural network") that receives at least a component of the imaging data from the scanner system via the communication interface.

The image reconstruction system can further include a repository that stores a training data set and/or images collected from use of an imaging modality system (e.g., quantitative transmission ultrasound systems) over time for training or self-learning of the neural network of the reconstruction engine.

In some cases, the system further includes a discriminator for use in training the one or more neural networks. For example, the repository can store a training set of reflection and transmission images and/or raw data The training or self-learning of the neural network can be accomplished by using the discriminator to compare the transmission data (corresponding to the reflection data) from the repository to the synthetic transmission data generated from the corresponding reflection data and output a set of errors that are used to adjust weights in the GAN-based algorithm for the neural network.

In some cases, one or more application programming interfaces can be provided as part of the image reconstruction system to support third party submission of training data and support third party submission of image reconstruction algorithms.

A method for image reconstruction can include receiving, at a reconstruction engine, imaging data; generating, using at least one GAN-based neural network, intermediate synthetic transmission data from at least a component of the imaging data; performing iterative methods on at least the intermediate synthetic transmission data until a desired accuracy is reached; and upon reaching the desired accuracy, outputting final synthetic transmission data. When the imaging data includes reflection data, an initial/intermediate synthetic estimate for a transmission image can be generated using a neural network and GAN-based algorithm (a "GAN-based neural network") that is trained (machine or self-learning) on imaging data (e.g., paired reflection and transmission data such as available via quantitative transmission ultrasound); and an iterative method for image reconstruction is performed using the initial/intermediate synthetic estimate to generate increasingly accurate transmission images until a desired accuracy is reached. In some cases, transmission data (e.g., of a conventional frequency range such as starting above 1.5 MHz) can be included with the received imaging data and the image reconstruction can be carried out using the transmission data and the initial/intermediate synthetic estimate. In some cases, two types of reflection data (e.g., a reflection image(s) and a set of reflection data) can be processed by GAN-based neural networks trained on the imaging data to create two types of initial/intermediate synthetic transmission data (e.g., a synthetic transmission image(s) and a set of synthetic transmission data). When only reflection data is received, the image reconstruction can be carried out using synthetic transmission data and the initial/intermediate synthetic estimate.

A method for training a neural network can include receiving training imaging data, the imaging data comprising paired transmission data and reflection data; generating, using a GAN-based neural network, synthetic transmission data from the reflection data; comparing transmission data that is paired with the reflection data with the synthetic transmission data to determine a set of errors; and adjusting weights of the GAN-based neural network using the set of errors. The method for training a neural network can further or alternatively include receiving paired transmission images and reflection images, generating using a GAN-based neural network, an initial guess of a synthetic transmission image from a reflection image; performing iterative methods using speed of sound data corresponding to a transmission image that is paired with the reflection image and the initial guess of the synthetic transmission image until a desired accuracy is reached; upon reaching the desired accuracy, outputting a final synthetic transmission image; comparing the transmission image that is paired with the reflection image with the final synthetic transmission image to determine a set of errors; and adjusting the weights of the GAN-based neural network using the set of errors.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DISCLOSURE

The application of machine learning or self-learning to iterative and multimodality image reconstruction is described. Iterative image reconstruction refers to the methods for the image reconstruction. Multimodality refers to the ability of using different types of input parameters for an image. For example, CT and MRI data may be used to reconstruct a MRI image; reflection data may be used to reconstruct a speed of sound image; or a first bandwidth range of data may be used to reconstruct an image covering a larger or different bandwidth range of data. The resulting output that may be of different modality or characteristics is referred to as "synthetic" output, which may be raw data or images. Synthetic information is information of a type that emulates the real information of that type but is either made from a different type of information or is of the same type but with different aspects (e.g., frequencies).

The ability to reconstruct images from suboptimal inputs as provided by certain embodiments of the described systems and techniques for "efficient" image reconstruction is highly advantageous. For example, certain embodiment of the described systems and techniques can allow for data received from cheaper, older, or more general machines to be used to reconstruct useful and detailed images. In some cases, mobile scanners can be used, and the more complex reconstruction can be carried out on separate systems such as described herein. The mobile scanners may be reflection ultrasound scanners and/or transmission ultrasound scanners with transmission frequencies above a certain threshold (e.g., starting between 800 kHz and 1.5 MHz). Transmission ultrasound scanners with larger frequency ranges (e.g., starting at lower frequencies such as 300 kHz) generally produce clearer and higher quality images; however, such transmission ultrasound scanners tend to require unconventional, finer or larger hardware to collect the transmission data, which often results in a more expensive machine. The described systems and techniques enable scanners of lower bandwidth to produce adequate images (which may be clearer or appear higher quality than what is usually able to be reconstructed from the data), which can further support availability of ultrasound images in a wide variety of applications and environments.

Indeed, in some cases, the described methods can be used to produce very rough scans, from relatively limited amount of data/projections, in a short period of time. This is especially useful as a real-time display while scanning (e.g., "scout scan") in order to aid in patient positioning. The scan can be cancelled in short order if the patient positioning is inadequate, and this could be determined quickly—far before the image would have been fully acquired and/or processed through more conventional means.

Figure 1:
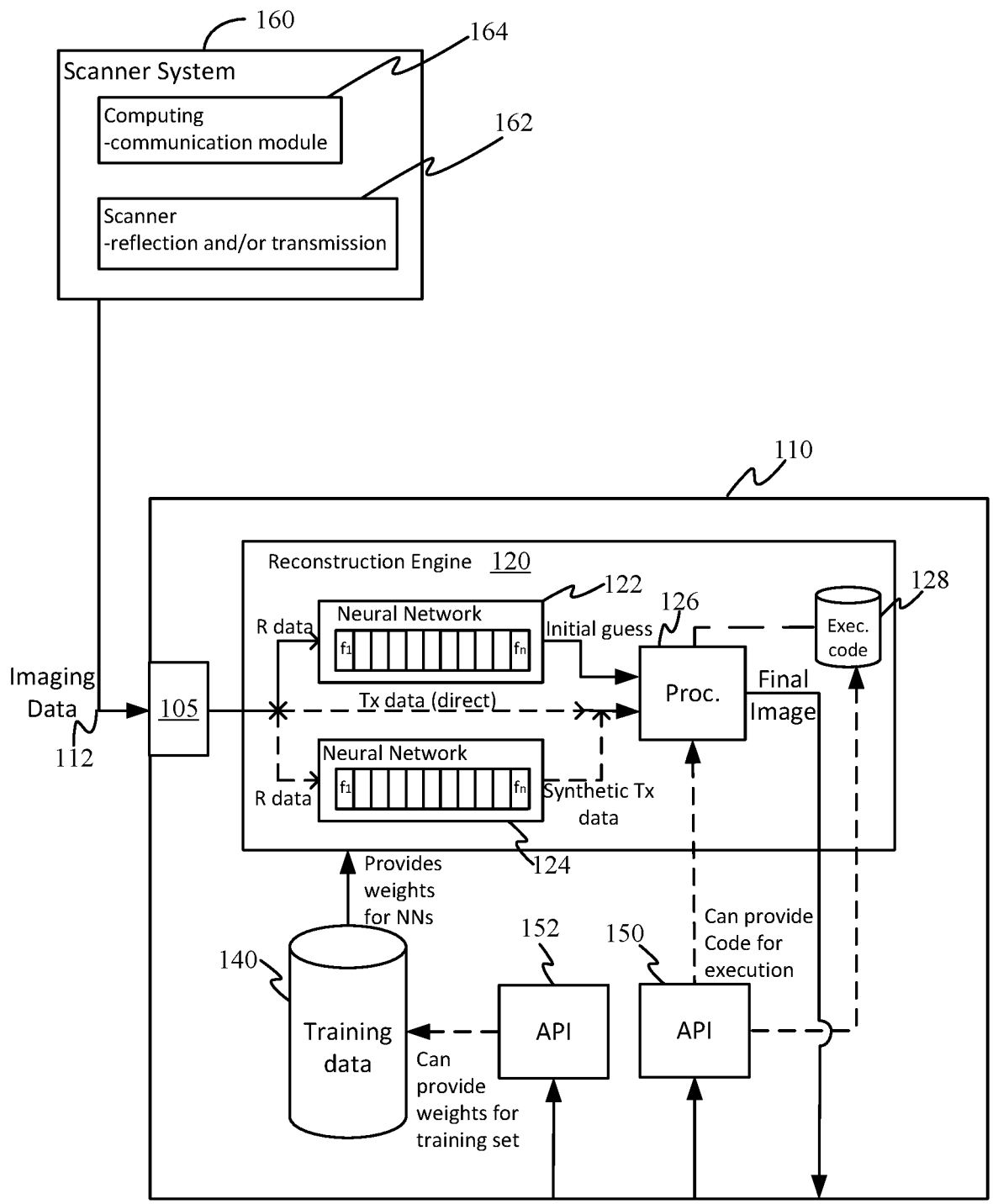
FIG. 1 illustrates an operating environment for machine learning based image reconstruction.

FIG. 1 illustrates an operating environment for machine learning based image reconstruction. Referring to FIG. 1, the operating environment can include an image reconstruction system 110. The system 110 can include a communication interface 105 that can receive imaging data 112 from a scanner system 160 and a reconstruction engine 120. The system 110 can further include a storage device 140 containing training data for a neural network of reconstruction engine 120 (e.g., neural networks 122, 124), and one or more APIs 150, 152.

The system 110 can be remote, cloud-based, or locally operated. Similarly, the components of the system can exist in the same space or some or all can be hosted in different locations (e.g., distributed). In some cases, inputted data can be streamed in real-time from a scanner system 160. In some cases, input data can be batch received or obtained post scan, for example, directly from a scanner system 160 or when the scanner system 160 transmits the input data to an intermediary system, which provides or makes available the data to the system 110 after completion of a scan (or parts of the scan). Interface 105 may be any suitable communications interface that can communicate wired or wirelessly with scanner system 160 directly or indirectly.

For ultrasound implementations, the system 110 can take in, depending on implementation, ultrasound data as input. Ultrasound data can include transmission data providing speed-of-sound and attenuation information and reflection data providing reflection information. Raw data or images may be received. The system 110 can, in other implementations, receive as input various other image datatypes, such as CT or MRI. The reconstruction engine 120 can be the part of the system that transforms the input (e.g., any of the image data described above) into the output of a reconstructed image. It should be understood that the system 110 is capable of using one imaging modality datatype (e.g., MRI) and output another synthetic imaging modality datatype (e.g., ultrasound) with the use of paired data, as is explained further below.

One method of machine learning based image reconstruction uses neural networks. Accordingly, the reconstruction engine 120 can include at least one neural network (such as one, both, or more than the two neural networks 122, 124 illustrated in FIG. 1), a processor 126, and a computer storage system 128 storing executable code, for example a reconstruction algorithm, that can be executed by processor 126.

The one or more neural networks 122, 124 can be Generative Adversarial Networks (GANs). Accordingly, at least one neural network includes a GAN-based algorithm that receives at least a component of the imaging data 112 from the communication interface 105.

The inputs to the reconstruction engine 120 as a whole can be directly input to the neural networks (e.g., neural networks 122, 124). In some cases, the inputs to the neural networks 122, 124 undergo data normalization and/or conversion from 3D volumes into 2D slices. Example implementations of reconstruction engines can be seen in FIGS. 2A and 2B.

The neural networks 122, 124 can utilize feature sets that serve to assist in transforming one or more images and/or datasets into another image and/or dataset. Features such as interfaces where the tissue/matter changes within a reflection image—for instance, skin and connective tissue elements such as Cooper's ligaments—have a large impact on defining boundaries within the generated speed-of-sound images (see also U.S. application Ser. No. 15/836,576, entitled "Color Coding An Image for Identifying Anatomy Using Quantitative Transmission Ultrasound Tomography", for identification of features. Particularly when a cyclical neural network, such as a CycleGAN is used, features such as interfaces between skin and water, dense and fatty tissue, cysts and solids, and physical tissue deformations in the presence of medical tape can be useful in generating reflection images (see also U.S. application Ser. No. 15/836,576, entitled "Color Coding An Image for Identifying Anatomy Using Quantitative Transmission Ultrasound Tomography", for identification of features).

Processor 126 can receive the output of the neural network(s) 122, 124 (and additionally, in some cases, possibly a direct input to the system 110, which may or may not have been used by reconstruction engine 120). Via execution of executable code, the processor 126 can perform image reconstruction, for example, via iterative methods for image reconstruction.

In some cases, the at least one neural network includes two neural networks (e.g., neural networks 122, 124) and the imaging data 112 received via interface 105 is reflection data and a reflection image. The described neural networks can be used to estimate a transmission image from a reflection image, which serves a similar purpose to low frequency transmission data in providing a starting point for image reconstruction to be tuned by higher frequencies.

For example, one neural network 124 receives the reflection data and generates a set of synthetic transmission data from the reflection data. The other neural network 122 receives the reflection image and generates an intermediate synthetic transmission image from the reflection image. The instructions for performing image reconstruction, when executed by the processor 126, then direct the processor 126 to at least: perform iterative methods on the set of synthetic transmission data and the intermediate synthetic transmission image until a desired accuracy is reached, and upon reaching the desired accuracy, output a final synthetic transmission image.

A similar method can also be used if both reflection and transmission data are available to produce a superior image by using the latest image produced in each iteration to perform a check on the corresponding other image. For example, the imaging data 112 can be high frequency transmission data and a reflection image. The at least one neural network (e.g., neural network 122) receives the reflection image and generates an intermediate synthetic transmission image from the reflection image. The instructions for performing image reconstruction, when executed by the processor 126, then direct the processor 126 to at least: perform iterative methods on the high frequency transmission data and the intermediate synthetic transmission image until a desired accuracy is reached, and upon reaching the desired accuracy, output a final synthetic transmission image.

As can be seen from the examples illustrated above, the inputs of the processor 126 can be an initial guess of the image that is provided from the output of one of the neural network(s) 122, 124, transmission data, and/or reflection data. The output of the processor 126 can be the final image.

Example methods for image reconstruction can incorporate inverse scattering techniques, such as but not limited to the techniques described in "3-D Nonlinear Acoustic Inverse Scattering: Algorithm and Quantitative Results" (Wiskin et al., IEEE Transactions on Ultrasonics, Ferroelectrics, and Frequency Control, Vol. 64, No. 8, August 2017).

In some cases, image generation/reconstruction can use the neural network(s) to selectively remove and/or replace relatively higher noise (or low signal to noise ratio) image data at certain frequencies and/or viewing angles.

In some cases, the neural network(s) can be tuned to selectively improve and/or enhance the image quality of a certain tissue type or a region of interest. For example, use of a neural-network can selectively enhance the visibility of region with microcalcifications. In some of these cases, image quality in the rest of the breast tissue may become worse. In these cases, the enhanced visibility in the region with the microcalcifications may be merged with the original image (minus the corresponding region with the microcalcifications in the original image) to create an enhanced image. However, in some cases, the image quality in the rest of the breast tissue does not become worse and therefore does not need to be merged with the original image.

In some cases, system 110 can include an application programming interface (API) 150 enabling third parties to provide reconstruction algorithms (e.g., in the form of executable code) used by the reconstruction engine (e.g., processor 126). This API 150 can be considered an image reconstruction selector API. In some cases, the image reconstruction selector API can be used to receive an image reconstruction algorithm for execution by the processor. In some cases, the image reconstruction selector API can be used to select an existing available image reconstruction algorithm for execution by the processor. In some cases, the image reconstruction selector API supports extensibility of the reconstruction engine for use in image reconstruction of the data/images generated by the neural networks by other parties.

The storage device 140 can store training data used to generate weights for the neural network(s) 122, 124 of the reconstruction engine 120. The training data can be the sources of the weighting for the features (e.g., interfaces such as skin and water, dense and fatty tissue, cysts and solids, and physical tissue deformations in the presence of medical tape, and/or skin and connective tissue elements such as Cooper's ligaments) used by the neural networks in the system.

A variety of imaging modalities may be used as input data to teach the GAN-based algorithm to generate speed or reflection images. Such modalities include, but are not limited to, Transmission Ultrasound, Reflection Ultrasound, CT, MRI, PET, X-ray, SPECT, X-ray Mammography or any combination of multi-modalities. The system can create final images of these datatypes as the outputs. It may be desirable for such input data (i.e., training sets) to be obtained from scanning systems capable of correlating two or more imaging modalities (e.g., provide "paired data"). The correlation may be in terms of spatial and/or temporal dimensions between the provided paired data.

The training data itself can either be sourced externally or produced internally. In some cases, the output of the reconstruction engine 120 may be fed back to the system for self-learning. A possible methodology for obtaining training data from paired data is described in FIG. 4. In some cases, system 110 includes an API 152 for submitting images for use to train the neural networks 122, 124 of the reconstruction engine 120 or possibly for direct implementation of weights for the neural networks 122, 124. This API 152 can be considered a training data API. The training data API receives training data or weights for use in training the neural network.

In addition to APIs 150, 152, other APIs may be available. An API is an interface implemented by a program code component or hardware component (hereinafter "API-implementing component") that allows a different program code component or hardware component (hereinafter "API-calling component") to access and use one or more functions, methods, procedures, data structures, classes, and/or other services provided by the API-implementing component. An API can define one or more parameters that are passed between the API-calling component and the API-implementing component.

The API is generally a set of programming instructions and standards for enabling two or more applications to communicate with each other and is commonly implemented over the Internet as a set of Hypertext Transfer Protocol (HTTP) request messages and a specified format or structure for response messages according to a REST (Representational state transfer) or SOAP (Simple Object Access Protocol) architecture.

The data used in the system 110 can be collected via a device such as scanner system 160, which can also be considered an optional part of the system. The scanner system 160 can be a machine that includes a scanner 162 that takes ultrasound, MRI, or CT readings. If the scanner system 160 is an ultrasound scanner, reflection data and, optionally, transmission data can be collected. For transmission ultrasound scanner implementations, the scanner system 160 can take readings in at least the 800 kHz to 1.5 MHz range. The scanner system 160 can include a communication module 164 for communicating with system 110 (or an intermediate system) to provide image data to the system 110. The scanner system 160 can also optionally include a storage system for storage of scanned data if the data is not streamed live.

Figure 2A:
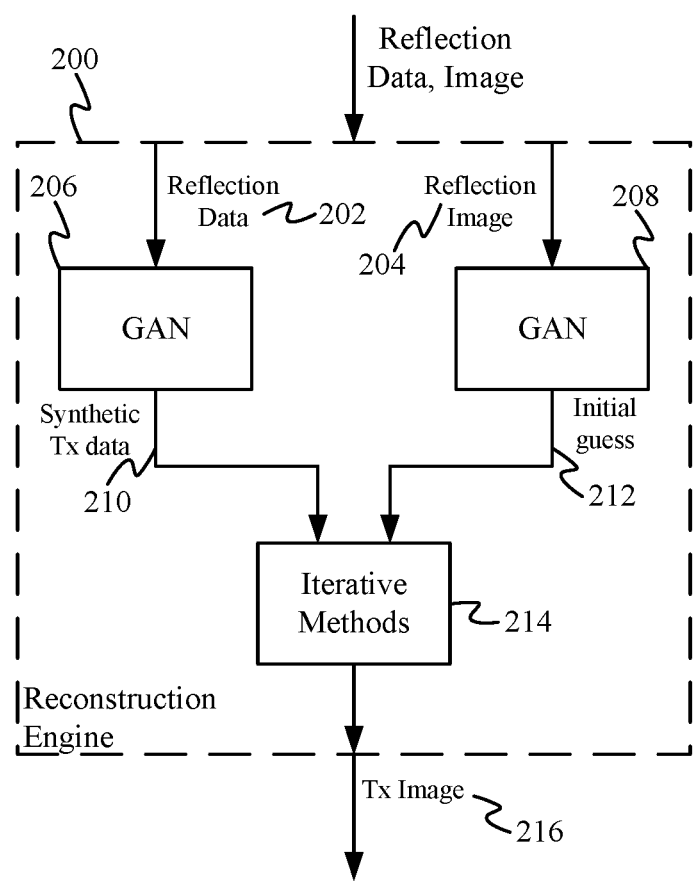
FIGS. 2A and 2B illustrate example reconstruction engine configurations.
Figure 2B:
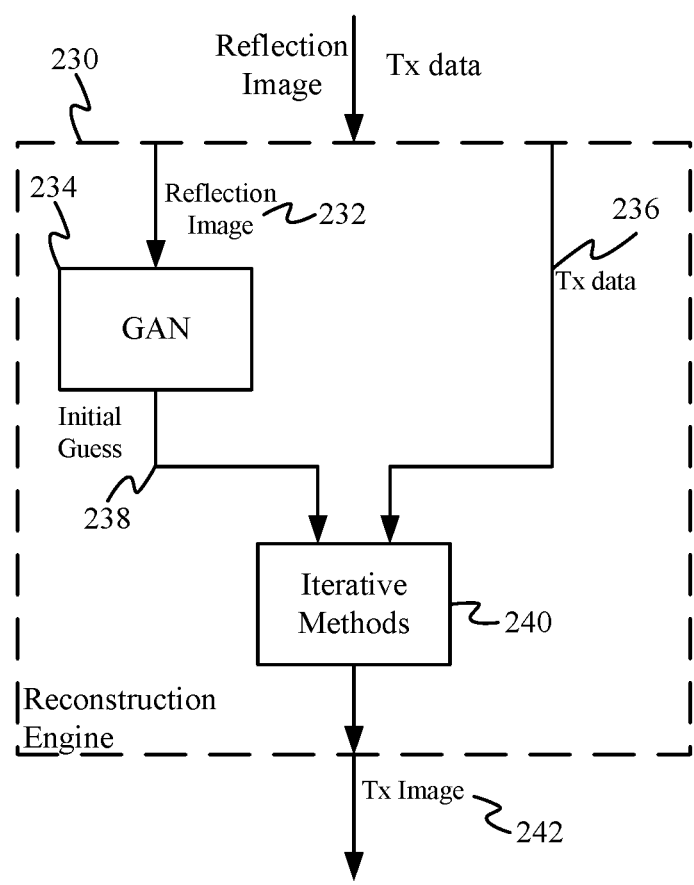

FIGS. 2A and 2B illustrate example reconstruction engine configurations. FIG. 2A illustrates an implementation using only reflection data, and FIG. 2B illustrates an implementation using reflection data along with transmission data. In both examples, the reconstruction engine can perform a method including receiving imaging data; generating, using at least one GAN-based neural network, intermediate synthetic transmission data from at least a component of the imaging data; performing iterative methods on at least the intermediate synthetic transmission data until a desired accuracy is reached; and upon reaching the desired accuracy, outputting final synthetic transmission data.

FIG. 2A illustrates a reconstruction engine 200 for an input set of imaging data that includes only reflection data (which can be in the form of both raw reflection data and a reflection image) that generates intermediate synthetic transmission data of both a set of synthetic transmission data and an initial guess for a transmission image and outputs a synthetic transmission image as the final synthetic transmission data.

A reconstruction engine 200 that includes only reflection data as input and outputs a synthetic transmission image is useful because a reflection data input set represents something of a barebones setup—a system that produces only reflection data can be cheaper, as an entire sensor array is excluded. Alternatively, a reconstruction engine 200 that includes only reflection data as input and outputs a synthetic transmission image could be used for diagnostic purposes in the 10 mm region (e.g., for imaging areas where the angle for that type of imaging modality is difficult to support transmission through the tissue), as transmission data is difficult to collect at this scale. For example, it can be difficult to capture information in the interface from a patient's chest cavity to the patient's breast.

The reflection image 204 can be created through traditional means (prior to receipt at the reconstruction engine 200 or by a component of the reconstruction engine that is not shown in the figure), and the transmission data that one otherwise might not be able to obtain could be constructed through this process. A neural network 206 can receive the reflection data 202 and output a set of synthetic transmission data 210 for the same scanned object, while another neural network 208 can receive the reflection image 204 as input and can output an initial guess for the transmission image 212. The processor (e.g., processor 126 of FIG. 1) can receive the initial guess for the transmission image 212 and the set of synthetic transmission data 210, execute the code (e.g., in the form of a reconstruction algorithm) that performs the iterative methods 214, and produce a final transmission image 216.

Accordingly, a reconstruction method can include generating, using a first GAN-based neural network, an intermediate set of synthetic transmission data from the reflection data; generating, using a second GAN-based neural network, an intermediate synthetic transmission image (the initial guess) from the reflection image; and performing iterative methods on the intermediate set of the synthetic transmission data and the intermediate synthetic transmission image until a desired accuracy is reached in order to output a final synthetic transmission image.

FIG. 2B illustrates a reconstruction image 230 for an input set of imaging data that includes transmission data in addition to the reflection data (which can be in the form of either raw reflection data that is then used to generate a reflection image through traditional means or is received in the form of the reflection image) and that generates intermediate synthetic transmission data of an initial guess for a transmission image and outputs a transmission image as the final synthetic transmission data. The transmission data can possibly be limited to only relatively high frequencies, such as starting at 800 kHz to 1.5 MHz. This can be useful because low frequency data requires finer and often more expensive or bulkier equipment. The methodology as a whole has advantages over existing implementations, even when the low frequency transmission data is available. Since the reflection image can be used to create an initial estimate for the transmission image fairly quickly (e.g., 10 seconds, 30 seconds, 1 minute, 5 minutes; for example, an estimate may be possible within 1-2 minutes for a typical breast size), the amount of time the system takes to reach a final estimate is cut down. To implement this methodology, one neural network 234 can receive the reflection image 232 as input and output an initial guess for the transmission image 238. This image can be used, along with the received transmission data 236, as an input for the processor (e.g., processor 126 of FIG. 1) that executes the code that performs the iterative methods 240. The output can be the final transmission image 242.

Accordingly, a reconstruction method can include generating, using one GAN-based neural network, an intermediate synthetic transmission image (the initial guess) from the reflection image; and performing iterative methods on the intermediate synthetic transmission image and received transmission data until a desired accuracy is reached in order to output a final synthetic transmission image.

Figure 3:
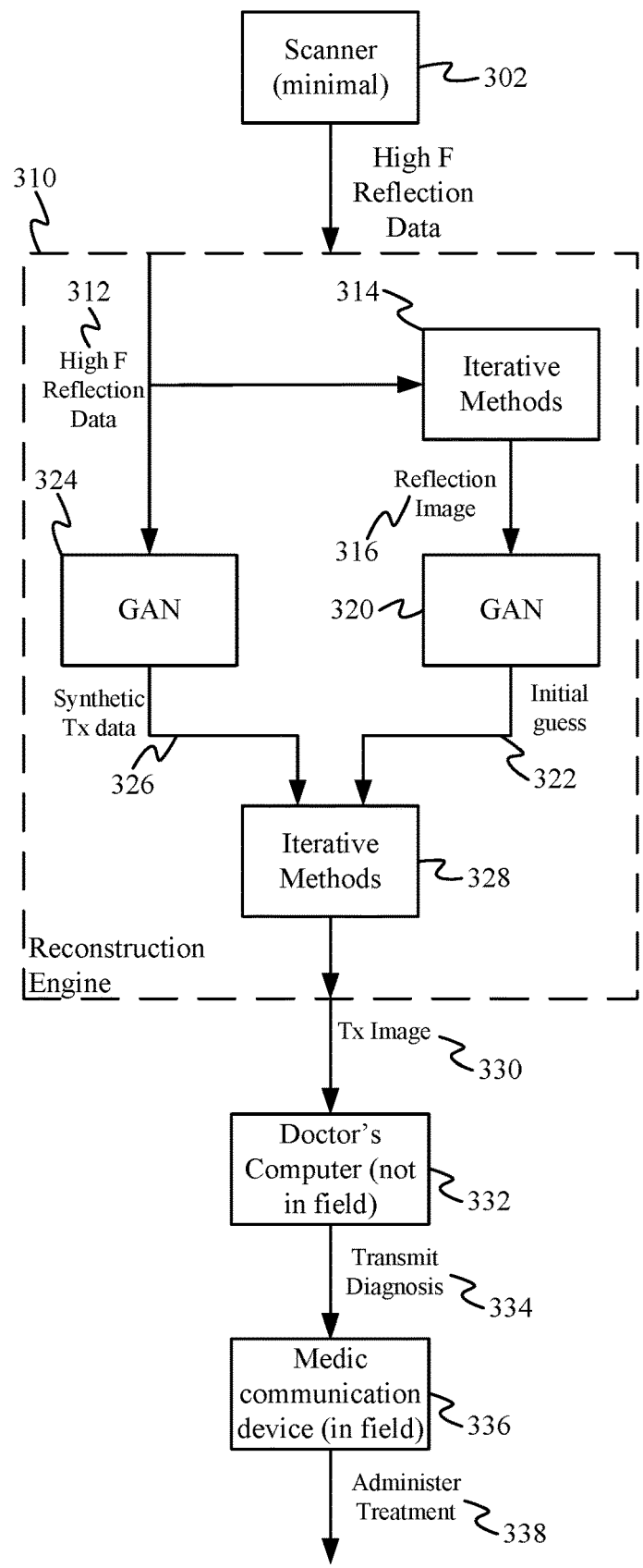
FIG. 3 illustrates an example scenario using machine learning based image reconstruction.

FIG. 3 illustrates an example scenario using machine learning based image reconstruction. The environment described is a combat scenario, where medics can quickly and accurately provide treatment to soldiers using ultrasound analysis with minimal equipment. A soldier might be injured in the field, prompting a medic to use a simple ultrasound device 302. This device may only gather reflection data 312, as transmission data requires an extra receiver, and may only acquire high frequency data, as low frequency data requires a more complicated and often less portable device. This data can be collected and sent to the cloud (or to a server implementing the described recognition engine located nearby or remotely). A reconstruction engine 310, such as described with respect to 120 of FIG. 1, 200 of FIG. 2A, or 230 of FIG. 2B, can use the high-frequency reflection data 312 received directly from the ultrasound device 302 or indirectly (e.g., via a computing system that can communicate over a network) as an input to perform iterative methods 314 to generate an intermediate reflection image 316. Then, a neural network 320 generates an initial guess for the transmission image 322 using the intermediate reflection image 316. A separate neural network 324 can receive the high-frequency reflection data 312 as an input to produce a set of synthetic transmission data 326. The synthetic transmission data 326 and the initial guess for the transmission image 322 are taken as inputs to an iterative method 328, which produces the finalized transmission image 330. An army doctor, not in the field, can receive these images on the doctor's computer 332. The doctor can make a recommendation (e.g., diagnosis) for treatment based on the images and forward 334 the recommendation to the medic (e.g., via a communication device 336), who can carry out (338) the instructions, possibly without ever leaving the field. Communication device 336 can be a phone, computer, or other device that can receive audio or visual input.

Figure 4:
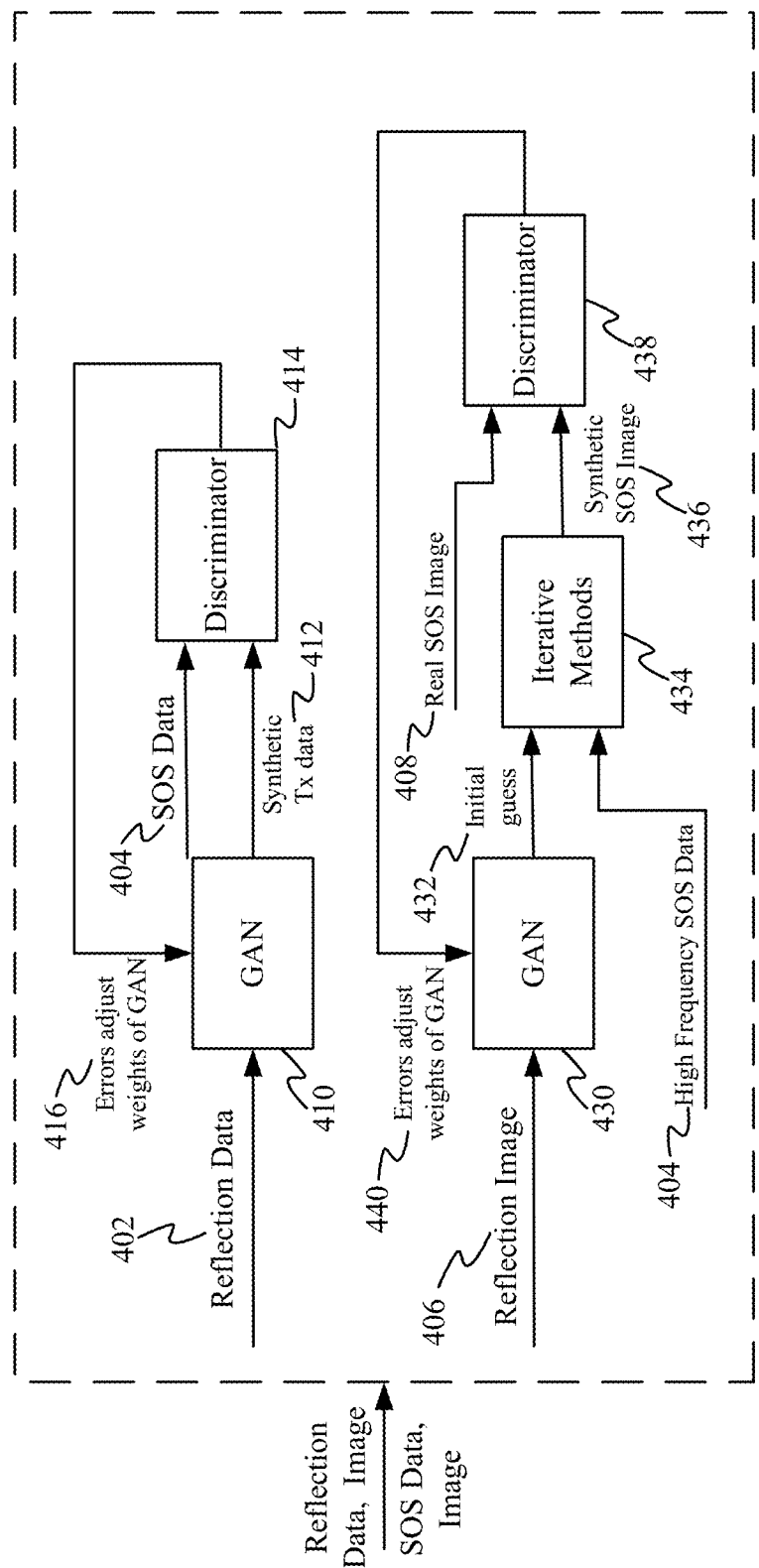
FIG. 4 illustrates an example process for training a feature set of a neural network using paired data.

FIG. 4 illustrates an example process for training a feature set of a neural network using paired data. The process can be implemented within an image recognition system such as image recognition system 110 described with respect to FIG. 1. In some cases, one or more discriminators can be included for use in training the one or more neural networks 122, 124. Turning to the example in FIG. 4, for a certain dataset, there can exist both reflection and transmission data and images for a 3D volume position corresponding to a certain scanned object. The set of transmission and reflection data at each individual position in the 3D image space can be considered a set of paired data, as each (spatial and/or temporal) point in the reflection data can correspond to a single point in the transmission data. For transforming reflection data into synthetic transmission data, a neural network 410 can take in reflection data 402 as an input. The output synthetic transmission data 412 can be compared against the input transmission data 404 using a discriminator 414 that outputs a set of errors 416 that can be used to adjust the weights of the neural network. This process can occur iteratively, until a neural network that adequately constructs a set of synthetic data that is sufficiently close (e.g., within a range of error that comes to a resolution/resolves, etc.) to the corresponding paired data. The neural network 410 can also be trained across multiple datasets (e.g., using paired data from different imaging modalities) to find a set of weights that is most useful across all possible sets.

For training a neural network to transform a reflection image into a transmission image, a similar process can be employed. The neural network 430 to be trained can take the reflection image 406 as an input and output an initial guess 432 of a transmission image. A set of iterative methods 434 can receive the transmission data 404 (possibly including only the high frequency data) and the initial guess 432 of the transmission image to output a synthetic transmission image 436. A discriminator 438 can compare the synthetic transmission image to the real transmission image 408 and produce a set of errors 440 that can be used to adjust the weights of the neural network. This process can occur iteratively, until a neural network that adequately constructs a synthetic transmission image that is sufficiently close to the corresponding paired image. The neural network 430 can also be trained across multiple datasets to find a set of weights that is most useful across all possible sets.

Another method of training can involve a GAN-based algorithm called CycleGAN. CycleGAN can be used to generate speed images from reflection images and vice-versa. Based on paired transmission and reflection images, CycleGAN can learn how to convert a speed image into a reflection image, and a reflection image into a speed image, at the same time. The algorithm can employ a concept where a discriminator function is used to minimize the error in the conversion from speed, to reflection, and back to speed again. The source of this error can be determined by the discriminator and the weights and features for the CycleGAN can be modified to reduce the error in future iterations. Further, at the same time, an attempt can be made to minimize the error in the conversion from reflection, to speed, and back to reflection again.

The training of the neural network can occur in two dimensions or three dimensions. Training in three dimensions can allow for the neural network to better differentiate between tissues as well as learn about tissue connectivity. For instance, adjacent voxels with similar values can be searched in three dimensions to more easily distinguish between tissues. This approach can improve differentiation between anatomy, for example, between ligaments and other elements that may have similar values, but not similar shapes.

Using paired training leaves open the possibility for a very strong and flexible system. If two systems have data that can be paired and are related at all, it is possible to train the neural network transform one into another. If the paired data exists at runtime—in other words, if the system is presented with paired data such as ultrasound and MRI—the two can be used together to refine the model more quickly and accurately than if the two were to be run by neural networks without paired data, as you create two models for testing in a single cycle.

The use of paired data can also be useful when using exclusively ultrasound data. If both reflection and transmission data is present, the system can compare the results of each iteration in the iterative methods to the results of the other iteration. The comparison can lead to improving the speed of the formation of the final image by comparing the two and using the commonalities as a stronger basis for the initial image used for the next iteration. Accordingly, a method for training a neural network can include receiving training imaging data, the imaging data comprising paired transmission data and reflection data; generating, using a GAN-based neural network, synthetic transmission data from the reflection data; comparing transmission data that is paired with the reflection data with the synthetic transmission data to determine a set of errors; and adjusting weights of the GAN-based neural network using the set of errors.

In some cases, in addition to or as an alternative, the method can include receiving paired transmission images and reflection images, generating using a GAN-based neural network, an initial guess of a synthetic transmission image from a reflection image; performing iterative methods using speed of sound data corresponding to a transmission image that is paired with the reflection image and the initial guess of the synthetic transmission image until a desired accuracy is reached; upon reaching the desired accuracy, outputting a final synthetic transmission image; comparing the transmission image that is paired with the reflection image with the final synthetic transmission image to determine a set of errors; and adjusting the weights of the GAN-based neural network using the set of errors. Initial weights for the neural networks can be received via a training data application programming interface such as described with respect to API 152 of FIG. 1.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A system comprising:
    a communication interface receiving imaging data from a scanner system; and
    a reconstruction engine comprising:
        at least one neural network that includes a GAN-based algorithm that receives at least a component of the imaging data from the communication interface;
        a processor; and
        storage media storing instructions for performing image reconstruction using an output of the at least one neural network when executed by the processor,
    wherein the at least one neural network comprises two neural networks;
    wherein the imaging data is reflection data and a reflection image;
    wherein one of the two neural networks receives the reflection data and generates a set of synthetic transmission data from the reflection data; and
    wherein the other one of the two neural networks receives the reflection image and generates an intermediate synthetic transmission image from the reflection image.

2. The system of claim 1, wherein the instructions for performing image reconstruction, when executed by the processor, direct the processor to at least:
    perform iterative methods on the set of synthetic transmission data and the intermediate synthetic transmission image until a desired accuracy is reached; and
    upon reaching the desired accuracy, output a final synthetic transmission image.

3. The system of claim 1, further comprising an image reconstruction selector application programming interface (API), wherein the image reconstruction selector API receives an image reconstruction algorithm for execution by the processor.

4. The system of claim 1, further comprising a training data application programming interface (API), wherein the training data API receives training data or weights for use in training the neural network.

5. A system comprising:
    a communication interface receiving imaging data from a scanner system; and
    a reconstruction engine comprising:
        at least one neural network that includes a GAN-based algorithm that receives at least a component of the imaging data from the communication interface;
        a processor; and
        storage media storing instructions for performing image reconstruction using an output of the at least one neural network when executed by the processor,
    wherein the imaging data is high frequency transmission data and a reflection image; and
    wherein the at least one neural network receives the reflection image and generates an intermediate synthetic transmission image from the reflection image.

6. The system of claim 5, wherein the instructions for performing image reconstruction, when executed by the processor, direct the processor to at least:
    perform iterative methods on the high frequency transmission data and the intermediate synthetic transmission image until a desired accuracy is reached; and
    upon reaching the desired accuracy, output a final synthetic transmission image.

7. The system of claim 5, further comprising an image reconstruction selector application programming interface (API), wherein the image reconstruction selector API receives an image reconstruction algorithm for execution by the processor.

8. The system of claim 5, further comprising a training data application programming interface (API), wherein the training data API receives training data or weights for use in training the neural network.

9. A system comprising:
    a communication interface receiving imaging data from a scanner system; and
    a reconstruction engine comprising:
        at least one neural network that includes a GAN-based algorithm that receives at least a component of the imaging data from the communication interface;
        a processor; and
        storage media storing instructions for performing image reconstruction using an output of the at least one neural network when executed by the processor,
    wherein the reconstruction engine further comprises a discriminator and a repository of corresponding reflection and transmission data;
    wherein a neural network of the at least one neural network receives reflection data and generates synthetic transmission data; and
    wherein the discriminator compares transmission data corresponding to the reflection data to the synthetic transmission data and outputs a set of errors that are used to adjust weights in the GAN-based algorithm for the neural network.

10. The system of claim 9, further comprising an image reconstruction selector application programming interface (API), wherein the image reconstruction selector API receives an image reconstruction algorithm for execution by the processor.

11. The system of claim 9, further comprising a training data application programming interface (API), wherein the training data API receives training data or weights for use in training the neural network.

12. A system comprising:
    a communication interface receiving imaging data from a scanner system; and
    a reconstruction engine comprising:
        at least one neural network that includes a GAN-based algorithm that receives at least a component of the imaging data from the communication interface;
        a processor; and storage media storing instructions for performing image reconstruction using an output of the at least one neural network when executed by the processor, further comprising a discriminator and a repository of corresponding reflection and transmission images;

wherein a neural network of the at least one neural network receives a reflection image and generates a synthetic transmission image; and wherein the discriminator compares a transmission image corresponding to the reflection image to the synthetic transmission image and outputs a set of errors that are used to adjust weights in the GAN-based algorithm.

* * * * *